United States Patent
Hopper et al.

(10) Patent No.: US 10,643,744 B2
(45) Date of Patent: May 5, 2020

(54) DRUG DELIVERY DEVICE STATE RECOGNITION

(71) Applicant: West Pharmaceutical Services, Inc., Exton, PA (US)

(72) Inventors: Kevin Hopper, Athens, TX (US); Stacy Faught, Scottsdale, AZ (US); Christopher Evans, Long Valley, NJ (US); Brian Costello, Whitehouse Station, NJ (US); Raymond Protasiewicz, Whippany, NJ (US)

(73) Assignee: West Pharmaceutical Services, Inc., Exton, PA (US)

( * ) Notice: Subject to any disclaimer, the term of this patent is extended or adjusted under 35 U.S.C. 154(b) by 0 days.

(21) Appl. No.: 15/999,805

(22) PCT Filed: Feb. 22, 2017

(86) PCT No.: PCT/US2017/018974
§ 371 (c)(1),
(2) Date: Aug. 20, 2018

(87) PCT Pub. No.: WO2017/147202
PCT Pub. Date: Aug. 31, 2017

(65) Prior Publication Data
US 2019/0341136 A1    Nov. 7, 2019

Related U.S. Application Data

(60) Provisional application No. 62/327,127, filed on Apr. 25, 2016, provisional application No. 62/306,411, (Continued)

(51) Int. Cl.
*G06Q 90/00*    (2006.01)
*G16H 20/17*    (2018.01)
(Continued)

(52) U.S. Cl.
CPC ............. *G16H 20/17* (2018.01); *A61M 5/31* (2013.01); *A61M 5/3204* (2013.01);
(Continued)

(58) Field of Classification Search
CPC ........ G06Q 50/24; G16H 50/20; G16H 10/60; G16H 50/30; G06F 19/3456;
(Continued)

(56) References Cited

U.S. PATENT DOCUMENTS

2008/0243088 A1    10/2008    Evans
2014/0357304 A1    12/2014    Ostrander et al.
(Continued)

FOREIGN PATENT DOCUMENTS

EP    2708253 A1    3/2014

OTHER PUBLICATIONS

Int'l Search Report and Written Opinion dated Jun. 14, 2017 in Int'l Appn. PCT/US17/18974.

*Primary Examiner* — Jamara A Franklin
(74) *Attorney, Agent, or Firm* — Panitch Schwarze Belisario & Nadel LLP (57)    ABSTRACT

A method of detecting and/or tracking use of a drug delivery device is disclosed. The drug delivery device includes a machine readable code and a visual indicator, and has pre-use and used states, such that use of the drug delivery device triggers a transition from the pre-use to the used state. The visual indicator has a first state when the drug delivery device is in the pre-use state and a different second state when the drug delivery device is in the used state. The method includes enabling a user device having an image sensor to capture an image of the drug delivery device, determining, by the user device processor from the captured image, whether the visual indicator of the drug delivery device is in the second state, and obtaining, by the processor,
(Continued)

information from the machine readable code when the visual indicator is determined to be in the second state.

12 Claims, 6 Drawing Sheets

Related U.S. Application Data filed on Mar. 10, 2016, provisional application No. 62/298,229, filed on Feb. 22, 2016.

(51) Int. Cl.
*A61M 5/31* (2006.01)
*A61M 5/32* (2006.01)
*G06K 7/10* (2006.01)
*G06K 7/14* (2006.01)
*G06K 9/00* (2006.01)

(52) U.S. Cl.
CPC ......... *A61M 5/326* (2013.01); *G06K 7/10722* (2013.01); *G06K 7/1413* (2013.01); *G06K 9/00664* (2013.01); *A61M 2005/3267* (2013.01); *A61M 2205/18* (2013.01); *A61M 2205/3306* (2013.01); *A61M 2205/3592* (2013.01); *A61M 2205/6054* (2013.01); *A61M 2205/6072* (2013.01); *A61M 2205/6081* (2013.01)

(58) Field of Classification Search
CPC ............ G06F 19/3418; G06F 19/3462; A61M 2205/583; A61M 2205/584; A61M 2205/50; A61J 2205/20; A61J 2205/30
USPC .............................. 235/375, 462.01; 604/189
See application file for complete search history.

(56) References Cited

U.S. PATENT DOCUMENTS

| | | |
|---|---|---|
| 2015/0209114 A1 | 7/2015 | Burkholz et al. |
| 2015/0209510 A1 | 7/2015 | Burkholz et al. |
| 2017/0368263 A1* | 12/2017 | Ploch ..................... G16H 20/17 |

* cited by examiner

DRUG DELIVERY DEVICE STATE RECOGNITION

CROSS-REFERENCE TO RELATED APPLICATIONS

This application is a section 371 of International Application No. PCT/US17/18974, filed Feb. 22, 2017, which was published Aug. 31, 2017 under International Publication No. WO 2017/147202 A1, which claims the benefit of U.S. Provisional Application No. 62/327,127, filed Apr. 25, 2016, U.S. Provisional Application No. 62/306,411, filed Mar. 10, 2016 and U.S. Provisional Application No. 62/298,229, filed Feb. 22, 2016, the disclosures of which are incorporated herein by reference.

BACKGROUND OF THE INVENTION

Embodiments of the present invention are directed to drug delivery devices, and more particularly, to a method for accurately detecting and reporting self-administration of a drug delivery device.

Many patients are required to self-administer medications, such as through self-injection devices, inhalers, or other like drug delivery devices. Often, it is important that the patient adhere to particular dosing schedules in order for treatment to be effective. With the widespread use of smartphones, patients are able to record and even report, to doctors or other like healthcare entities, individual dosage administrations. In many cases, patients can not only record and report the time a dose is administered, but the name of the medication, the dosage amount, and other like, relevant data. This enables medical professionals to better track patient adherence. Some companies even establish rewards programs that offer incentives to patients to adhere to their medication schedule by tracking their dosage administrations with their smartphones.

However, it can be difficult to determine whether the medication has actually been taken by the patient. For example, some applications require the patient to manually enter information using their smartphones, which creates an opportunity for false reporting. Similarly, some drug delivery devices have been equipped with bar codes or other machine readable tags that can be scanned by the smartphone to enable the recording and reporting. While more convenient than manual data entry, the machine readable codes also generally do not provide more certainty as to whether the drug delivery device had actually been used. Attempts have been made to rectify this issue, such as through the use of RFID tags which become activated upon use of the drug delivery device. Yet, such methods typically require costly and burdensome modifications to the drug delivery device by the manufacturer.

It is therefore desirable to provide a method for enabling a patient to record and report medication schedule adherence while reliably ensuring that the drug delivery device being reported has actually been used, without the need for significant modification to the actual drug delivery device. It is further desirable to also provide healthcare facilities with a method for tracking administration of medications to patients by its doctors, nurses, and the like.

BRIEF SUMMARY OF THE INVENTION

An embodiment of the present invention comprises a method of detecting and/or tracking use of a drug delivery device. The drug delivery device includes a machine readable code and a visual indicator, and has a pre-use state and a used state, such that use of the drug delivery device triggers a transition from the pre-use state to the used state. The visual indicator has a first state when the drug delivery device is in the pre-use state and a different second state when the drug delivery device is in the used state. The method includes enabling a user device having an image sensor to capture one or more images of the drug delivery device, determining, by a processor of the user device from at least one of the one or more captured images, whether the visual indicator of the drug delivery device is in the second state, and obtaining, by the processor of the user device, information from the machine readable code when the visual indicator is determined to be in the second state.

Another embodiment of the present invention comprises a method of detecting and/or tracking use of a drug delivery device. The drug delivery device includes a machine readable code and has a first shape in a pre-use state and a different second shape in a used state, such that use of the drug delivery device triggers a transition from the pre-use state to the used state. The method includes enabling a user device having an image sensor to capture one or more images of the drug delivery device, determining, by a processor of the user device from at least one of the one or more captured images, whether the drug delivery device has the second shape, and obtaining, by the processor of the user device, information from the machine readable code when the drug delivery device is determined to have the second shape.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Certain terminology is used in the following description for convenience only and is not limiting. The words "right," "left," "lower" and "upper" designate directions in the drawings to which the reference is made. The words "inwardly" and "outwardly" refer to directions toward and away from, respectively, the geometric center of the apparatus and designated parts thereof. The terminology includes the words above specifically mentioned, derivatives thereof and words of similar import.

Figure 1A:
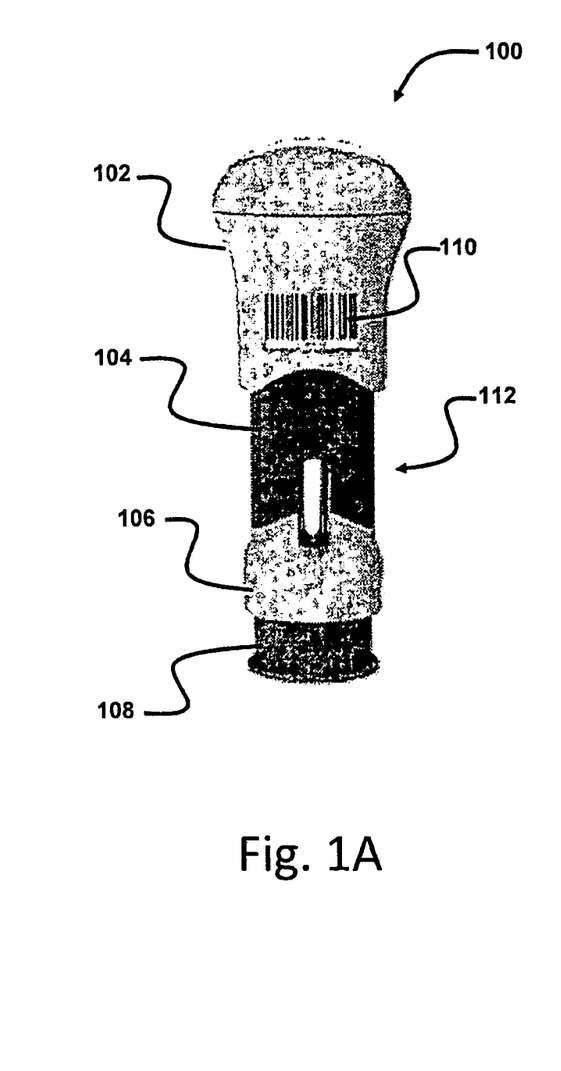
FIG. 1A is a front side elevational view of a drug delivery device in an unused state in accordance with a first preferred embodiment of the present invention.
Figure 1B:
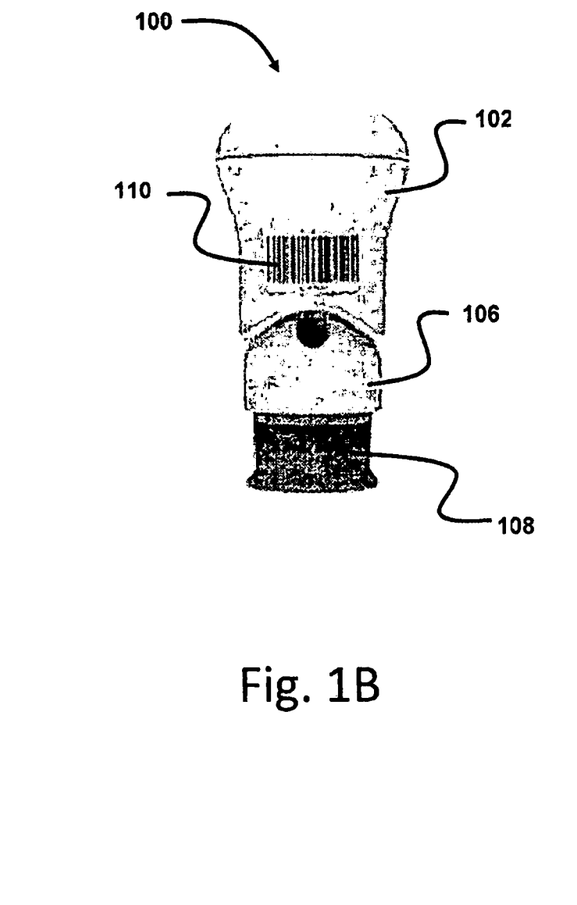
FIG. 1B is a front side elevational view of the drug delivery device of FIG. 1A in the used state.

Referring now to FIGS. 1A and 1B, there is shown a drug delivery device 100 in unused and used states, respectively, in accordance with a first preferred embodiment of the invention. The drug delivery device 100 in FIGS. 1A and 1B is shown as a palm-activated injector, but this is exemplary only, and other types of drug delivery devices, such as pen injectors, auto-injectors, syringes, inhalers, and the like can be used in connection with the present invention as well.

The drug delivery device 100 includes an upper housing 102, a middle housing 104, and a lower housing 106. In the unused state, shown in FIG. 1A, the upper housing 102 partially overlies a proximal portion of the middle housing 104, and a distal-most portion of the middle housing 104 is fixedly seated on the lower housing 106. A syringe (not shown) is housed within the drug delivery device 100, preferably the syringe is fixedly held within the lower housing 106, while the upper housing 102 is utilized to actuate a plunger of the syringe to administer the injection. A needle guard 108 is exposed from a distal end of the lower housing 106 and is movable with respect thereto. When a user presses the needle guard 108 against the skin, the needle guard 108 retracts into the lower housing 106, exposing a needle (not shown) of the syringe. The needle guard 108 is preferably biased by a spring (not shown) to return to its original position following the injection and removal from the skin. A locking mechanism (not shown) also preferably prevents the needle guard 108 from being retracted again following use. In the used state (FIG. 1B), the upper housing 102 preferably completely overlies the middle housing 104, and is preferably prevented from being moved proximally with respect to the lower housing 106. Thus, use of the drug delivery device 100 triggers a transition from the pre-use state (FIG. 1A) to the used state (FIG. 1B).

The user may be the patient, in which case the drug is self-administered. In other embodiments, the user may be a healthcare professional, such as a doctor, nurse, or the like, who administers the drug to the patient.

The drug delivery device 100 further preferably includes a machine readable code 110. The machine readable code 110 is preferably an optically readable code (e.g., a one-dimensional barcode, stacked barcode, a PDF417 code, a QR code, or other two- or three-dimensional barcodes, or the like), although other types of machine readable codes, such as passive or active electromagnetic tags (e.g., RFID tag, NFC tag, or the like), combinations thereof, or the like can be used as well. The machine readable code 110 preferably includes at least one of an identification of the drug in the drug delivery device 100, an identification of the make or type of the drug delivery device 100, a date of manufacture (or expiration date) of the drug and/or the drug delivery device 100, and the like. Preferably, the machine readable code 110 has a unique identifier so that a user cannot rescan the same drug delivery device 100 to report multiple injections.

The machine readable code 110 in FIGS. 1A and 1B is disposed on an exterior surface of the drug delivery device 110, particularly the upper housing 102, although other suitable locations may be used as well. In this way, the machine readable code 110 remains visible when the drug delivery device 100 is in the used state to allow for scanning. The machine readable code 110 may be printed directly on the drug delivery device 100, or may be part of a label adhered, molded, or otherwise fixed to the drug delivery device 100. For machine readable codes 110 that do not require visibility, such as RFID tags or the like, the machine readable code 110 may be embedded in or hidden by one or more components of the drug delivery device 110.

The drug delivery device 100 further includes a visual indicator 112, which has a first state when the drug delivery device 100 is in the unused state, and a second state when the drug delivery device 100 is in the used state. In some embodiments, including the one shown in FIGS. 1A-1B, the visual indicator 112 is a color or image that is provided on at least one component of the drug delivery device 100. For example, in FIG. 1A, the visual indicator 112 is a color of the middle housing 104, which is preferably highly distinct from the rest of the drug delivery device 100. For example, a drug delivery device 100 that is mainly white and gray may have the middle housing 104 colored blue. In the unused state of FIG. 1A, the visual indicator 112 has a first state, meaning that the color of the middle housing 104 is visible. In the used state, the visual indicator 112 has a second state, i.e., the color of the middle housing 104 is obscured by the upper housing 102. Thus, the drug delivery device 100 can be easily distinguished between the used and unused states, as will be described in more detail below.

The visual indicator 112 does not require that the entire middle housing 104 include the distinct color, only a portion is necessary to provide the distinction between the used and unused states of the overall drug delivery device 100. In addition, components other than, or in addition to, the middle housing 104 can include the visual indicator 112. Moreover, the visual indicator 112 can, rather than being a simple color, be any type of recognizable and distinguishable image. In addition, while the visual indicator 112 in FIG. 1B is hidden when the drug delivery device 100 is in the used state, the opposite can be true. For example, the visual indicator 112 can be hidden when the drug delivery device 100 is in the unused state, and become visible when the drug delivery device 100 moves to the used state.

Figure 2A:
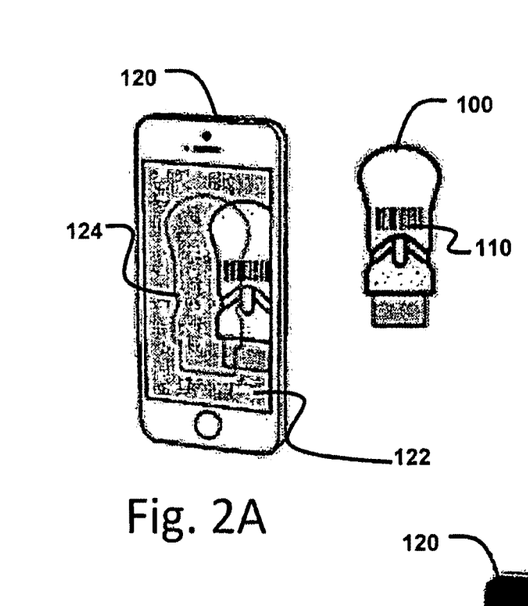
FIG. 2A is a schematic view of a user device attempting to capture an image of the device of FIG. 1B.
Figure 2B:
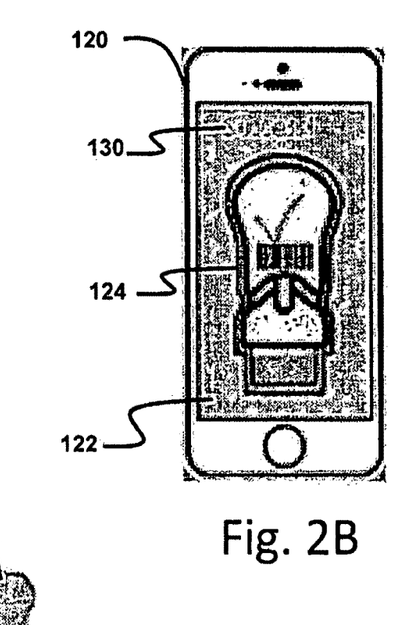
FIG. 2B is a schematic view of the user device of FIG. 2B showing success in obtaining data from a machine readable code on the drug delivery device of FIG. 1B.
Figure 2C:
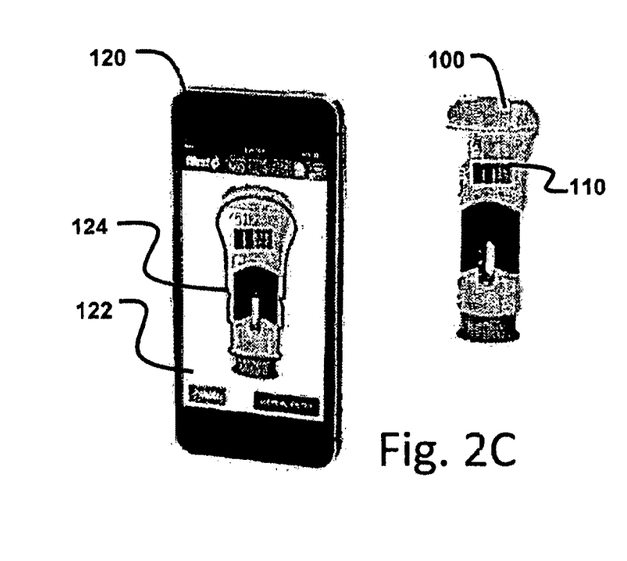
FIG. 2C is a schematic view of the user device of FIG. 2A following an unsuccessful attempt to obtain data from the machine readable code on the drug delivery device of FIG. 1A.

Referring now to FIGS. 2A-2C, operation of the method for detecting and/or tracking use of the drug delivery device 100 will now be explained. Preferably, a user downloads or accesses over a network an application using a user device 120 having a processor (not shown) for executing the application. The user device 120 is preferably a smartphone or other mobile or personal computing device, preferably with an image sensor (not shown) for capturing one or more images of the drug delivery device 100. For instances where the machine readable code 110 is an electromagnetic tag, the user device 120 is preferably equipped with the appropriate circuitry, such as RFID or NFC reader circuitry (not shown). In addition, the application may enable, or the user device 120 may already include, optical code (e.g., bar code) reading functionality.

The application preferably allows the user to capture one or more images of the drug delivery device 100 for analysis. For example, the user can, using a display 122 of the user device 120 as a viewfinder, align the image sensor to capture images of the drug delivery device 100. To assist the user, a visual device outline 124, which preferably corresponds to a shape of the drug delivery device 100 in the used state, may be provided on the display 122. Thus, the user will align the visual device outline 124 with the drug delivery device 100 prior to image capture. Image capture may be automatic upon proper alignment of the visual device outline 124 and the drug delivery device 100. Alternatively, the user may be prompted to press a button, touch the display 122, or the like to manually initiate image capture. In other instances, the user may be able to capture images outside of the application and import the images from memory.

Once one or more images of the drug delivery device 100 are captured, the application then analyzes at least one of the images to determine whether the visual indicator 112 is in the second state. Image analysis can be carried out using conventional techniques for locating and identifying specified features, including colors, shapes, text, codes, and the like. In the example of FIGS. 2A-2C, it is determined whether the color of the middle housing 104 is present in the image. If the visual indicator 112 is determined to be in the second state, the application will proceed to obtain the information from the machine readable code 110. In one embodiment, the application analyzes one of the previously captured images of the drug delivery device 100 to locate and read the machine readable code 110. In other embodiments, the application may prompt the user to obtain a second image with the user device 120 in order to obtain the information from the machine readable code 110. In embodiments where the machine readable code 110 is an electromagnetic tag, the application may automatically initiate reading. In some embodiments, the user device 120 may substantially simultaneously read information from the machine readable code 110 during image capture (for example, a bar code may be decoded immediately following capture of the image of the drug delivery device), and the obtaining step would constitute validation of the read information following confirmation that the visual indicator 112 is in the second state.

Upon determining that the visual indicator 112 is in the second state, such as in FIG. 2B when the color of the middle housing 104 is obscured by the top housing 102, the application may present an alert 130 that the scan was successful. The alert 130 can include text, symbols (such as a check mark), a change in color in the visual device outline 124, combinations thereof, or the like. Upon a successful scan, the application may automatically save and/or send data locally or over wireless or wired networks to necessary recipients, such as doctors or other healthcare providers. Alternatively, the application may present another step where the user manually initiates the sending of the requisite data.

If the visual indicator 112 is not found to be in the second state, such as in FIG. 2C, where the colored middle housing 104 is still visible, the application may alert the user that the information from the machine readable code 110 cannot be obtained, and may instruct the user to use the device prior to scanning. In FIG. 2C, the visual device outline 124 changes color to red to indicate that scanning was unsuccessful. However, other types of alerts, such as by text, symbols, combinations thereof, or the like, can be used as well.

Figure 3A:
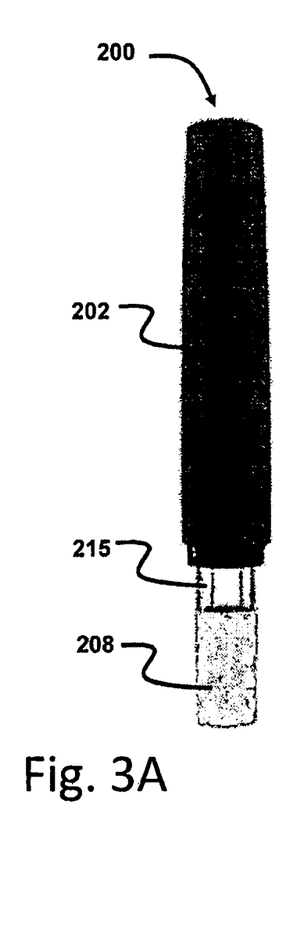
FIG. 3A is a front side elevational view of a drug delivery device in an unused state in accordance with a second preferred embodiment of the present invention.
Figure 3B:
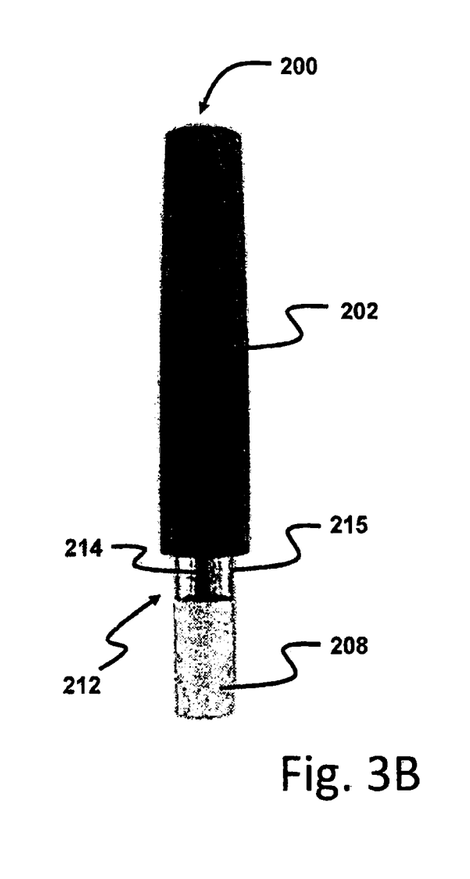
FIG. 3B is a front side elevational view of the drug delivery device of FIG. 3A in the used state.

FIGS. 3A and 3B show a drug delivery device 200 in accordance with a second preferred embodiment of the present invention. The drug delivery device 200 shown is an auto-injector having an upper housing 202 and a needle guard 208. The visual indicator 212 is a plunger rod 214 of the syringe (not shown) contained within the drug delivery device 200. In the pre-use state (FIG. 3A), the plunger rod 214 is not visible, but after use (FIG. 3B) the plunger rod 214 can be seen through a window 215 in the needle guard 208. An image of the drug delivery device 200 would therefore be analyzed to determine whether the plunger rod 214, as the visual indicator 212, is in the second state (i.e., visible) in order to confirm usage of the drug delivery device 200.

Figure 4A:
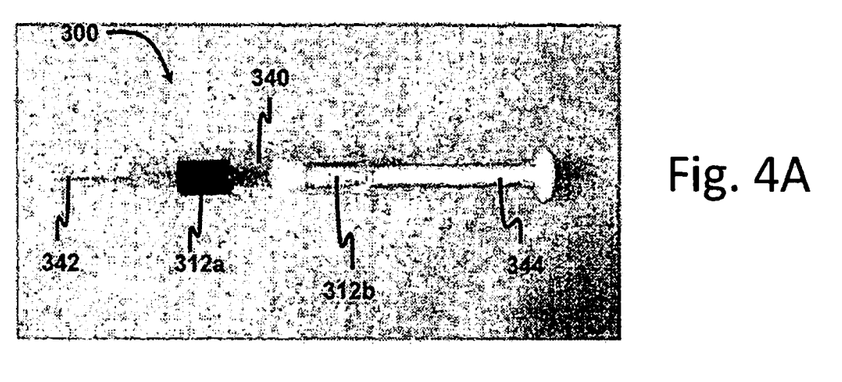
FIG. 4A is a front side elevational view of a drug delivery device in an unused state in accordance with a third preferred embodiment of the present invention.
Figure 4B:
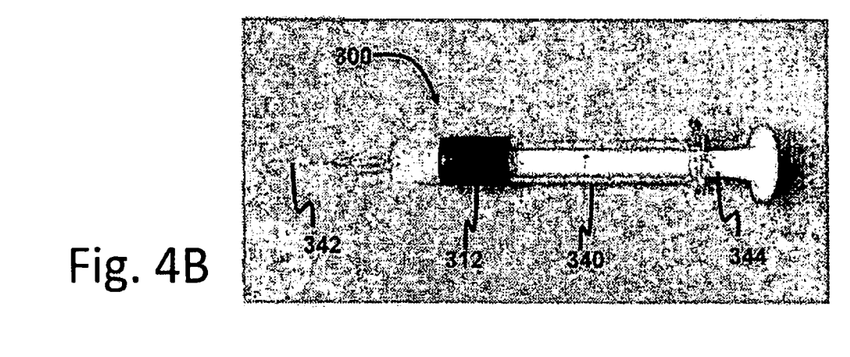
FIG. 4B is a front side elevational view of the drug delivery device of FIG. 4A in the used state.

FIGS. 4A and 4B show a drug delivery device 300 in accordance with a third preferred embodiment of the present invention. The drug delivery device 300 shown is a standard syringe having a barrel 340, a needle 342, and a plunger rod 344. The visual indicator 312 in FIGS. 4A and 4B is a two-part component. In the first state (FIG. 4A), a first, semitransparent colored ring 312*a* is visible on the barrel 340, while a second semitransparent colored ring 312*b* is visible around the plunger rod 344, with the first and second plunger rods 312*a*, 312*b* being axially separated from one another. After the drug delivery device 300 is actuated to the used state (FIG. 4B)—i.e., the injection has been completed—the first and second colored rings 312*a*, 312*b* are coaxial with one another, such that the two colors blend together. For example, the first ring 312*a* may be blue and the second ring 312*b* may be yellow, such that when the visual indicator 312 is in the second state, the two rings 312*a*, 312*b* combine to make green. Accordingly, the application on the user device would determine whether green appears in the image of the drug delivery device 300.

Figure 5A:
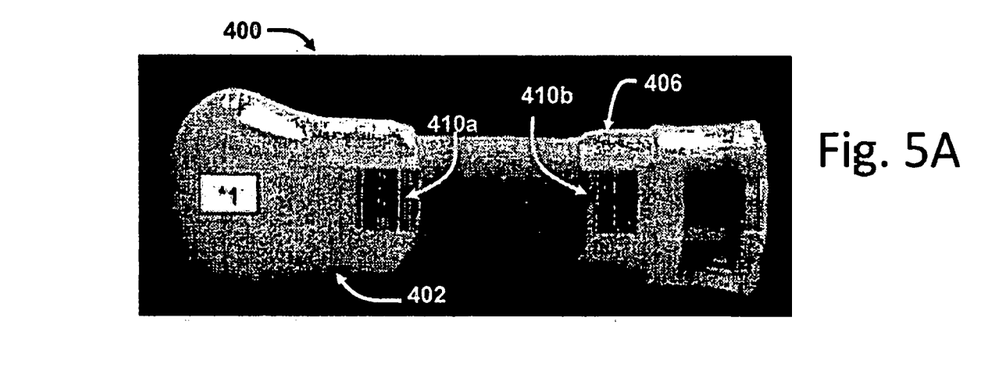
FIG. 5A is a front side elevational view of a drug delivery device in an unused state in accordance with a fourth preferred embodiment of the present invention.
Figure 5B:
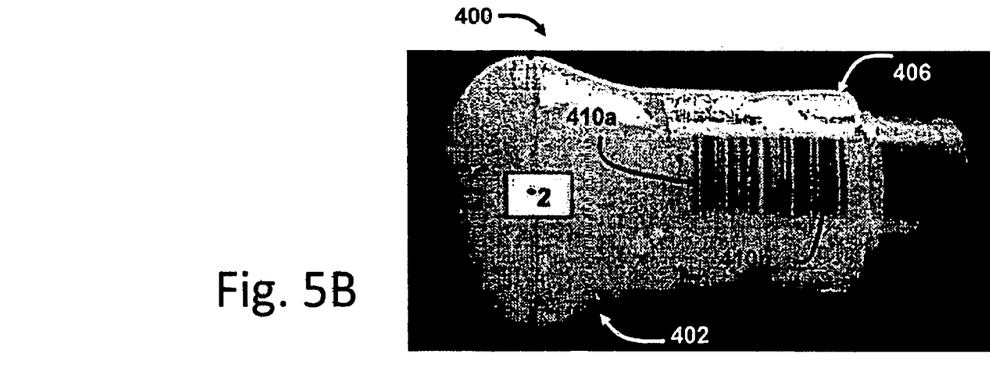
FIG. 5B is a front side elevational view of the drug delivery device of FIG. 5A in the used state.

FIGS. 5A and 5B show a drug delivery device 400 in accordance with a fourth preferred embodiment of the present invention. The drug delivery device 400 is again shown as a palm-activated injector. The present embodiment differs slightly from previous embodiments in that an additional measure is added to prevent reading of the machine readable code 410 prior to use of the drug delivery device 400. In particular, the machine readable code 410 is a bar code or other type of optical code that is split into at least two portions 410*a*, 410*b* prior to use of the drug delivery device 400. In FIG. 5A, one portions of the machine readable code 410*a* is disposed on the upper housing 402, while the other portion of the machine readable code 410*b* is disposed on the lower housing 406. Once the drug delivery device 400 is in the used state, the two portions of the machine readable code 410*a*, 410*b* are brought together, and can then be read. This technique can be used in the place of, or in combination with, the visual indicator methods described above.

Figure 6A:
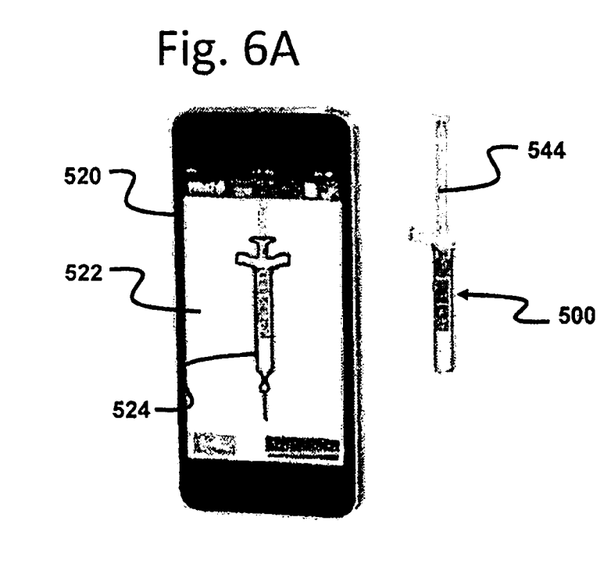
FIG. 6A is a schematic view of a user device following an unsuccessful attempt to scan a drug delivery device in an unused state in accordance with a fifth preferred embodiment of the present invention.
Figure 6B:
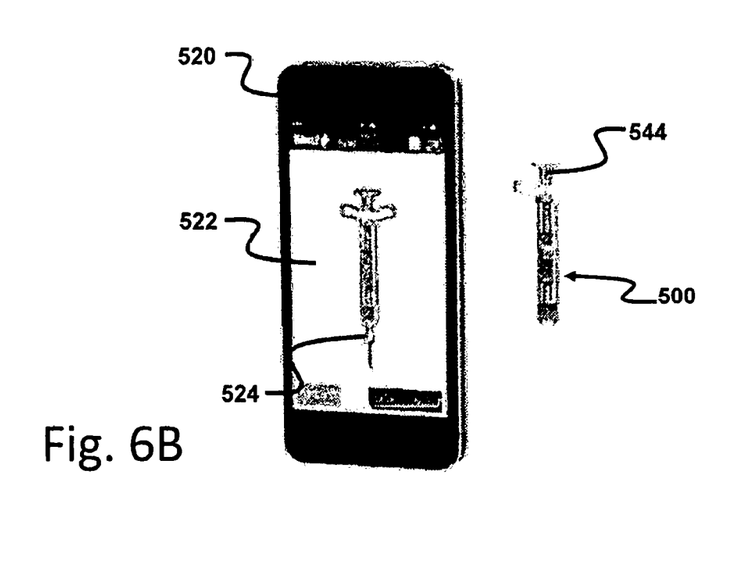
FIG. 6B is a schematic view of the user device of FIG. 6A following a successful attempt to scan the drug delivery device of FIG. 6A in the used state.

FIGS. 6A and 6B illustrate another method in accordance with a fifth preferred embodiment of the present invention. In addition to, or in place of, a visual indicator as described above, the shape of the drug delivery device 500 can be used to detect its state. For example, the drug delivery device 500 shown in FIG. 6A is a syringe in its unused state. The plunger rod 544 is fully extended proximally, such that the overall appearance of the drug delivery device 500 is elongated. In FIG. 6B, in the used state, the plunger rod 544 is fully depressed, significantly shortening the length of the drug delivery device 500. With shape recognition, the application running on the user device 520 will only obtain and accept information from the drug delivery device 500 if the used shape is recognized from the images. This method can be aided with the use of the visual device outline 524 on the display 522 of the user device 520.

For example, in FIG. 6A, with the drug delivery device 500 in the unused state, the form factor of the drug delivery device 500 does not match the visual device outline 524, and therefore images captured by the user device 520 will not result in a successful scan. However, in FIG. 6B, the plunger rod 544 is depressed and the shape of the drug delivery device 500 matches the visual device outline 524. As before, information from a machine readable code (not shown in FIGS. 6A, 6B) can thereafter be obtained and recorded/relayed as appropriate.

In all embodiments, the machine readable code can be used not only to provide information, but also to assist in imaging of the overall drug delivery device. For example, the machine readable code is preferably positioned to enable the user and/or the user device to determine that the drug delivery device is properly oriented for imaging purposes. The machine readable code can further be used for calibration of the application, since the dimensions thereof will generally be known, and can thereafter be used to reference the shape of the drug delivery device to determine if the drug delivery device is in the used state.

In some embodiments, the application may permit scanning both before and after use. For example, the machine readable code may be read by the user device prior to administration of the drug, for the purpose of obtaining drug or device information, instructions for use, or the like. After use, the application would preferably allow the machine readable code to be rescanned for a successful confirmation, gated by the requisite finding of the visual indicator or other indication of use, such as change in shape. In some embodiments, an additional machine readable code or other indicator (not shown) may be used for pre-use scanning. In some embodiments, the machine readable code may be altered by use of the drug delivery device to provide different results for pre- and post-use scans, For example, in the embodiment shown in FIGS. 5A and 5B, one or both portions of the machine readable code 410a, 410b may be scannable prior to use to obtain drug information, but only the combined machine readable code 410 can be scanned to confirm use. Other variations for permitting pre-use scanning can be used as well.

It will be appreciated by those skilled in the art that changes can be made to the embodiments described above without departing from the broad inventive concept of the invention. It is understood, therefore, that this invention is not limited to the particular embodiments disclosed, but it is intended to cover modifications within the spirit and scope of the present invention.

We claim:

1. A method of detecting or tracking use of a drug delivery device, the drug delivery device including a machine readable code and a visual indicator, the drug delivery device having a pre-use state and a used state, such that use of the drug delivery device triggers a transition from the pre-use state to the used state, wherein the visual indicator is a color or image provided on at least one component of the drug delivery device and has a first state when the drug delivery device is in the pre-use state and a different second state when the drug delivery device is in the used state, the method comprising:

enabling a user device having an image sensor to capture one or more images of the drug delivery device;

determining, by a processor of the user device from at least one of the one or more captured images, whether the visual indicator of the drug delivery device is in the second state by determining whether the color or image is present in the at least one of the one or more captured images; and obtaining, by the processor of the user device, information from the machine readable code in response to the determination that the visual indicator is in the second state.

2. The method of claim 1, wherein when the color or image is in the second state, the color or image is hidden by one or more additional components of the drug delivery device, and wherein the step of obtaining information from the machine readable code occurs only when the color or image is hidden in the at least one of the one or more captured images.

3. The method of claim 1, wherein when the color or image is in the first state, the color or image is hidden by one or more additional components of the drug delivery device, and wherein the step of obtaining information from the machine readable code occurs only when the color or image is visible in the at least one of the one or more captured images.

4. The method of claim 1, wherein the machine readable code is a bar code disposed on an exterior surface of the drug delivery device, and wherein the step of obtaining the information includes reading, by the processor of the user device, the bar code from at least one of the one or more captured images.

5. The method of claim 1, wherein the machine readable code is a bar code disposed on an exterior surface of the drug delivery device, and wherein the step of obtaining the information includes capturing at least one second image of the drug delivery device and reading the bar code from at least one second image.

6. The method of claim 1, further comprising:

presenting, by the processor of the user device, an alert to the user that the information from the machine readable code cannot be obtained when the visual indicator is determined by the processor of the user device to be in the first state.

7. The method of claim 1, further comprising:

providing, by a processor of the user device on a display of the user device, a visual device outline corresponding to a shape of the drug delivery device in the used state, the visual device outline configured to aid the user in capturing the one or more images of the drug delivery device.

8. A method of detecting or tracking use of a drug delivery device, the drug delivery device including a machine readable code, the drug delivery device having a first shape in a pre-use state and a different second shape in a used state, such that use of the drug delivery device triggers a transition from the pre-use state to the used state, the method comprising:

enabling a user device having an image sensor to capture one or more images of the drug delivery device;

determining, by a processor of the user device from at least one of the one or more captured images, whether the drug delivery device has the second shape; and obtaining, by the processor of the user device, information from the machine readable code in response to the determination that the drug delivery device has the second shape.

9. The method of claim 8, wherein the machine readable code is a bar code disposed on an exterior surface of the drug delivery device, and wherein the step of obtaining the information includes reading, by the processor of the user device, the bar code from at least one of the one or more captured images.

10. The method of claim 8, wherein the machine readable code is a bar code disposed on an exterior surface of the drug delivery device, and wherein the step of obtaining the information includes capturing at least one second image of the drug delivery device and reading the bar code from at least one second image.

11. The method of claim 8, further comprising:
presenting, by the processor of the user device, an alert to the user that the information from the machine readable code cannot be obtained when the drug delivery device is determined by the processor of the user device to have the first shape.

12. The method of claim 8, further comprising:
providing, by a processor of the user device on a display of the user device, a visual device outline corresponding to the second shape of the drug delivery device, the visual device outline configured to aid the user in capturing the one or more images of the drug delivery device.

\* \* \* \* \*